United States Patent [19]

Grasselli et al.

[11] 4,162,234
[45] Jul. 24, 1979

[54] OXIDATION CATALYSTS

[75] Inventors: Robert K. Grasselli, Chagrin Falls; Dev D. Suresh, Macedonia; Harley F. Hardman, Lyndhurst, all of Ohio

[73] Assignee: The Standard Oil Company, Cleveland, Ohio

[21] Appl. No.: 812,072

[22] Filed: Jul. 1, 1977

Related U.S. Application Data

[63] Continuation of Ser. No. 490,532, Jul. 22, 1974, abandoned.

[51] Int. Cl.$^2$ .................. B01J 21/02; B01J 27/14; B01J 27/02; B01J 23/10
[52] U.S. Cl. ............................ 252/432; 252/437; 252/439; 252/462; 252/464; 252/468; 252/469; 252/470; 260/465.3
[58] Field of Search ............... 252/470, 432, 437, 462, 252/439, 464, 469, 469

[56] References Cited

U.S. PATENT DOCUMENTS

| | | | |
|---|---|---|---|
| 3,414,631 | 12/1968 | Grasselli et al. | 260/680 E |
| 3,642,930 | 2/1972 | Grasselli et al. | 260/680 E |
| 3,803,204 | 4/1974 | Grasselli et al. | 252/470 X |
| 3,825,502 | 7/1974 | Takenaka et al. | 252/456 |
| 3,951,861 | 4/1976 | Shiroishi et al. | 252/464 X |
| 3,956,181 | 5/1976 | Grasselli et al. | 252/462 X |
| 3,968,166 | 7/1976 | Shiroishi et al. | 252/437 X |
| 3,972,920 | 8/1976 | Ishii et al. | 252/470 X |
| 3,984,477 | 10/1976 | Kubo et al. | 252/470 X |
| 3,988,359 | 10/1976 | Saito et al. | 252/439 X |
| 4,001,317 | 1/1977 | Grasselli et al. | 252/470 X |
| 4,042,625 | 8/1977 | Matsuzawa et al. | 252/437 X |

*Primary Examiner*—Delbert E. Gantz
*Assistant Examiner*—William G. Wright
*Attorney, Agent, or Firm*—John E. Miller, Jr.; Herbert D. Knudsen; Larry W. Evans

[57] ABSTRACT

Catalysts containing iron, bismuth, molybdenum plus nickel, cobalt, magnesium, zinc, cadmium, strontium or calcium are promoted with yttrium, zirconium, silver, sulfur, cerium, thorium, praseodymium, ruthenium, gallium, niobium, germanium, chromium, tin, manganese, indium, copper, tellurium, lanthanum, tantalum, tungsten or mixture thereof to give extremely desirable catalysts for various oxidation reactions.

21 Claims, No Drawings

OXIDATION CATALYSTS

CROSS REFERENCE TO RELATED APPLICATION

The present application is a continuation of Ser. No. 490,532 filed July 22, 1974 now abandoned.

BACKGROUND OF THE INVENTION

Catalysts that are improved upon by the present invention are known. See for example, U.S. Pat. No. 3,642,930 and U.S. Pat. No. 3,414,631. While these catalysts of the art are desirable oxidation catalysts, the catalysts of the invention have significant advantages over these other catalysts.

SUMMARY OF THE INVENTION

The present invention is oxidation catalysts of the formula $$X_a A_b D_c E_d Fe_f Bi_g Mo_{12} O_x$$

wherein
- X is yttrium, zirconium, silver, sulfur, cerium, thorium, praseodynium, ruthenium, gallium, niobium, germanium, chromium, tin, manganese, indium, copper, tungsten, tantalum, tellurium, lanthanum or mixture thereof;
- A is an alkali metal, thallium or mixture thereof;
- D is nickel, cobalt, magnesium, strontium, calcium, zinc, cadmium or mixture thereof;
- E is phosphorus, arsenic, boron, tungsten, antimony or mixture thereof; and wherein
- a is greater than 0 and less than 5;
- b and d are 0–4;
- c is 0.1 to 20;
- f and g are 0.1–10; and
- x is the number of oxygens required to satisfy the valence requirements of the other elements present.

In a particular embodiment of the invention, D is magnesium, calcium, silicon, zinc, cadmium or mixtures thereof when X is cerium, praseodynium or lanthanum. In another embodiment of the invention, D is strontium when X is silver, ruthenium or gallium.

In still another embodiment of the invention, E and X are so selected so that the catalyst contains a two or more element system selected from the group consisting of Mn+Sb, Mn+Cr, Pr+W and Mn+Ge.

The invention is any of the catalysts that are delimited by the formula above. These catalysts are prepared as shown in the specific embodiments and are useful for a wide range of known oxidation reactions. In these reactions, the new catalyst of the invention is substituted for the catalysts previously employed, and the reaction is conducted under substantially the same conditions. Of special interest is the oxidation, oxidative dehydrogenation of olefins, but other reactions such as the oxidation and ammoxidation of methyl substituted-aromatic compounds is also contemplated for these catalysts.

SPECIFIC EMBODIMENTS

EXAMPLES 1–9

Oxidative dehydrogenation of butene-1.

A reactor was constructed from a 0.8 cm. diameter stainless steel tube having an inlet for reactants and an outlet for products. The reactor had a reaction zone which could be charged with 2.5 cc. of catalyst.

Various catalysts of the invention were prepared as described below. All catalysts contained 80% active ingredients and 20% silica.

EXAMPLE 1

$Cr_{0.5}K_{0.1}Ni_{2.5}Co_{4.5}Fe_3BiMo_{12}O_x$

In 100 ml. of water, 63.56 g. of ammonium heptamolybdate, $(NH_4)_6Mo_7O_{24}.4H_2O$, was dissolved and 51.66 g. of Nalco 40% silica sol was added with stirring and heating. To this slurry was added 1.50 g. of $CrO_3$.

Separately, 36.36 g. of ferric nitrate, $Fe(NO_3)_3.9H_3O$, was heated and dissolved in 10 cc. of water. Then 14.55 g. $Bi(NO_3)_3.5H_2O$, 39.29 g. of $Co(NO_3)_2.6H_2O$, 21.81 g. of $Ni(NO_3)_2.6H_2O$ and 3.03 g. of a 10% solution of $KNO_3$ was dissolved in the solution. The nitrate solution was slowly added to the slurry containing the molybdenum. The mixture was heated and stirred until it began to thicken. The solid was dried in an oven at 120° C. with occasional stirring. The final catalyst was calcined in air at 550° C. for 16 hours.

EXAMPLE 2

$Te_{0.5}K_{0.1}Ni_{2.5}Co_{4.5}Fe_3BiMo_{12}O_x$

The catalyst was prepared in the same manner as shown in Example 1, except that 4.04 g. $TeCl_4$ was substituted for the $CrO_3$.

EXAMPLE 3

$Ge_{0.5}K_{0.1}Ni_{2.5}Co_{4.5}Fe_3BiMo_{12}O_x$

The catalyst was prepared in the same manner as Example 1, except that 1.57 g. of $GeO_2$ was substituted for the $CrO_3$.

EXAMPLE 4

$W_{0.5}K_{0.1}Ni_{2.5}Co_{4.5}Fe_3BiMo_{12}O_x$

The catalyst was prepared as described in Example 1, except that 4.04 g. of $(NH_4)_6W_7O_{24}.6H_2O$ was substituted for the $CrO_3$.

EXAMPLE 5

$Mn_{0.5}K_{0.1}Ni_{2.5}Co_{4.5}Fe_3BiMo_{12}O_x$

The catalyst was prepared as described in Example 1, except that 5.37 g. of a 50% solution of manganese nitrate was substituted for the $CrO_3$.

EXAMPLE 6

$Th_{0.5}K_{0.1}Ni_{2.5}Co_{4.5}Fe_3BiMo_{12}O_x$

The catalyst was prepared as shown in Example 1, except that 8.28 g. of $Th(NO_3)_4.4H_2O$ was substituted for the $CrO_3$.

EXAMPLE 7

$Nb_{0.5}K_{0.1}Ni_{2.5}Co_{4.5}Fe_3BiMo_{12}O_x$

In 50 cc. of warm water, 31.8 g. of ammonium heptamolybdate was dissolved. To this solution was added 2.0 g. of $NbCl_5$ slurried with water, 26.5 g. of Nalco 40% silica sol and a mixture of 10.9 g. of nickel nitrate and 19.7 g. cobalt nitrate.

Separately, a solution of 18.2 g. ferric nitrate, 7.2 g. of bismuth nitrate and 0.19 g. KOH as a 45% solution was prepared, and the solution was slowly added to the molybdenum slurry. The remainder of the preparation was the same as Example 1.

EXAMPLE 8

$Pr_{0.5}K_{0.1}Ni_{2.5}Co_{4.5}Fe_3BiMo_{12}O_x$

The catalyst was prepared as shown in Example 1, except that 2.60 g. of $PrO_2$ was substituted for the $CrO_3$.

EXAMPLE 9

$Ce_{0.5}K_{0.1}Ni_{2.5}Co_{4.5}Fe_3BiMo_{12}O_x$

The catalyst was prepared as described in Example 1, except that 8.22 g. of $(NH_4)_2Ce(NO_3)_6$ was substituted for the $CrO_3$.

The catalyst samples were ground and screened to give a 20 to 35 mesh fraction that was charged to the 2.5 cc. reaction zone of the reactor. A butene-1/air/steam feed of a molar ratio of 1/11/4 was fed over the catalyst at a temperature of 350° C. for an apparent contact time of one second.

The results of these experiments are stated in the following terms:

$$\% \text{ conversion} = \frac{\text{olefin reacted} \times 100}{\text{olefin fed}}$$

$$\% \text{ selectivity} = \frac{\text{product recovered} \times 100}{\text{olefin reacted}}$$

$$\% \text{ single pass yield} = \frac{\text{product recovered} \times 100}{\text{olefin fed}}$$

The results of these experiments are given in Table I. Isomerization of butene-1 is not computed as olefin reacted.

Table I

Oxidative Dehydrogenation of Butene-1 to Butadiene With $X_{0.5}K_{0.1}Ni_{2.5}Co_{4.5}Fe_3BiMo_{12}O_x$

| | | | Results, % | |
|---|---|---|---|---|
| Example | Catalyst, X= | Conversion | Selectivity to Butadiene | Single Pass Yield of Butadiene |
| 1 | Cr | 100 | 98 | 97.7 |
| 2* | Te | 98.8 | 98 | 97.3 |
| 3 | Ge | 98.8 | 98 | 96.8 |
| 4 | W | 98.6 | 96 | 95.7 |
| 5* | Mn | 98.4 | 97 | 95.2 |
| 6* | Th | 98.4 | 97 | 95.2 |
| 7 | Nb | 97.6 | 95 | 92.6 |
| 8* | Pr | 92.1 | 97.5 | 94 |
| 9* | Ce | 92.1 | 100 | 92 |

*no steam in feed

EXAMPLES 10-17

Oxidative dehydrogenation of butene-1 with germanium containing catalysts.

Various catalysts containing germanium were prepared as follows:

EXAMPLE 10

The catalyst was prepared the same as the catalyst of Example 1 except that no potassium was added and 1.57 g. $GeO_2$ was substituted for $CrO_3$.

EXAMPLE 11

The catalyst was prepared as shown in Example 10 except that the normal amount of potassium was added and 61.04 g. of nickel nitrate was used instead of the nickel and cobalt.

EXAMPLE 12

The catalyst was prepared as shown in Example 11 except that 61.12 g. of cobalt nitrate was substituted for the nickel nitrate.

EXAMPLE 13

The catalyst was prepared as shown in Example 11 except that 72.83 g. of ammonium heptamolybdate and 3.03 g. of a 45% KOH solution were used.

EXAAMPLE 14

The catalyst was prepared as shown in Example 11, except that 53.85 g. of $Mg(NO_3)_2 \cdot 6H_2O$ was added instead of the nickel and cobalt, and 3.22 g. of $GeCl_4$ was used in place of $GeO_2$.

EXAMPLE 15

The catalyst was prepared as shown in Example 11 except that magnesium nitrate was substituted for the nickel nitrate, and $GeCl_4$ was used as shown in Example 14.

EXAMPLE 16

The catalyst was prepared as shown in Example 11 except that manganese nitrate in the form of a 50% solution was substituted for the cobalt.

EXAMPLE 17

The catalyst was prepared as shown in Example 11 except that 2.72 g. of $GeCl_4$ was used for the germanium, 21.48 g. of a 50% solution of manganese nitrate replaced the nickel and 3.03 g. of a 45% solution of KOH were employed.

The catalysts were tested as shown in Examples 1–9. The results are shown in Table II.

Table II

Germanium-Containing Catalysts to Convert Butene-1 to Butadiene

| | | Results, % | | |
|---|---|---|---|---|
| Example | Catalyst | Conversion | Selectivity | Single Pass Yeild |
| 10 | $Ge_{0.5}Ni_{2.5}Co_{4.5}Fe_3BiMo_{12}O_x$ | 98.8 | 91 | 90.4 |
| 11 | $Ge_{0.5}K_{0.1}Ni_7Fe_3BiMo_{12}O_x$ | 99.9 | 94 | 94.3 |
| 12 | $Ge_{0.5}K_{0.1}Co_7Fe_3BiMo_{12}O_x$ | 87.4 | 99 | 86.8 |
| 13 | $Ge_{0.5}K_{0.8}Ni_{2.5}Co_{4.5}Fe_3BiMo_{13.75}O_x$ | 100.0 | 99 | 99.2 |
| 14 | $Ge_{0.5}K_{0.1}Mg_7Fe_3BiMo_{12}O_x$ | 98.7 | 98 | 96.8 |
| 15 | $Ge_{0.5}K_{0.1}Mg_{2.5}Co_{4.5}Fe_3BiMo_{12}O_x$ | 99.4 | 99 | 98.1 |
| 16 | $Ge_{0.5}K_{0.1}Ni_{2.5}Mn_{4.5}Fe_3BiMo_{12}O_x$ | 96.9 | 97 | 93.7 |
| 17 | $Ge_{0.4}K_{0.8}Mn_2Co_5Fe_3BiMo_{12}O_x$ | 55.2 | 99 | 54.6 |

EXAMPLE 18

Two promoters in thallium containing catalyst.

A catalyst of the formula 80% $Ge_{0.5}Cr_{1.5}Tl_{0.1}Ni_2Co_3Fe_{0.5}BiMo_{12}O_x$ and 20% $SiO_2$ was prepared in the same manner as described for the examples above and used in the oxydehydrogenation of butene-1 using a butene-1/air ratio of 1/11, a temperature of 350° C. and an apparent contact time of one second. The conversion of the butene-1 was 89.6%, the selectivity was 98% and the single pass yield was 88.1%.

EXAMPLE 19

Cesium containing catalyst.

A catalyst of the formula 80% $Mn_{0.5}Cs_{0.1}Ni_{2.5}Co_{4.5}Fe_3BiMo_{12}O_x$ and 20% $SiO_2$ was prepared as shown in Example 5 except that 0.59 g. cesium nitrate, $CsNO_3$, was substituted for the potassium compound. Using the feed and conditions of Example 18, butene-1 was 100% converted to products, the selectivity to butadiene was 99% and the single pass yield was 98.6%.

EXAMPLES 20–28

Oxydehydrogenation of butene-2.

Catalysts prepared in the examples above were used in the oxydehydrogenation of butene-2 to butadiene. Using the reactor, catalyst volumes of the examples above and an apparent contact time of one second, a mixture of 57.5% trans and 42.5% cis butene-2 was reacted. The ratio of butene-2/air was 1/11. The results of these experiments are given in Table III. The parenthesis around elements of the catalyst formula show elements copied in the later experiments.

Table III

| | | | Results, % | | |
|---|---|---|---|---|---|
| Example | Catalyst | Reaction Temp.,°C. | Conversion | Selectivity | Single Pass Yeild |
| 20 | $Ce_{0.5}(K_{0.1}Ni_{2.5}Co_{4.5}Fe_3BiMo_{12}O_x)$ | 350 | 95.4 | 93 | 88.3 |
| 21 | $Nb_{0.5}(K_{0.1}Ni_{2.5}Co_{4.5}Fe_3BiMo_{12}O_x)$ | " | 93.0 | 95 | 88.1 |
| 22 | $Pr_{0.5}(K_{0.1}Ni_{2.5}Co_{4.5}Fe_3BiMo_{12}O_x)$ | 375 | 97.7 | 89 | 87.3 |
| 23 | $Mn_{0.5}K_{0.1}Ni_{2.5}Co_{4.5}Fe_3BiMo_{12}O_x)$ | 385 | 95.1 | 93 | 88.9 |
| 24 | $Cr_{0.5}(K_{0.1}Ni_{2.5}Co_{4.5}Fe_3BiMo_{12}O_x)$ | " | 95.6 | 95 | 90.9 |
| 25 | $Ge_{0.5}(K_{0.1}Ni_{2.5}Co_{4.5}Fe_3BiMo_{12}O_x)$ | " | 84.4 | 95 | 80.5 |
| 26 | $W_{0.5}(K_{0.1}Ni_{2.5}Co_{4.5}Fe_3BiMo_{12}O_x)$ | " | 85.0 | 95 | 80.3 |
| 27 | $Th_{0.5}(K_{0.1}Ni_{2.5}Co_{4.5}Fe_3BiMo_{12}O_x)$ | 400 | 90.5 | 92 | 82.7 |
| 28* | $Ge_{0.5}K_{0.8}Ni_{2.5}Co_{4.5}Fe_3BiMo_{13.75}O_x$ | 375 | 95.7 | 90 | 86.5 |

*4 sec. contact time

EXAMPLES 29–37

Operation at high air-to-olefin ratios.

Catalysts of the invention prepared as described above were used to oxydehydrogenate a mixture of butene-2 in the same manner as shown for Examples 20–28, except that the butene-2/air ratio was 1/31. The reaction temperature was 350° C., and the apparent contact time was one second. The results of these experiments are shown in Table IV. The lanthanum catalyst of Example 37 was prepared by substituting 6.22 g. of $La(NO_3)_3.5H_2O$ for the $CrO_3$ in the catalyst of Example 1.

Table IV

Oxydehydrogenation of Butene-2 with Catalyst of $X_{0.5}K_{0.1}Ni_{2.5}Co_{4.5}Fe_3BiMo_{12}O_x$

| | | Results, % | | |
|---|---|---|---|---|
| Ex. | Catalyst, X= | Conversion | Selectivity | Single Pass Yield |
| 29 | Mn | 100.0 | 97 | 96.8 |
| 30 | Cr | 96.6 | 96 | 92.5 |
| 31[1] | Nb | 100.0 | 93 | 92.8 |
| 32 | Ce | 100.0 | 89 | 88.9 |
| 33[1] | Ce | 100.0 | 91 | 90.9 |
| 34 | Ge | 81.5 | 98 | 80.0 |
| 35[2] | W | 92.9 | 91 | 84.2 |
| 36[2] | Th | 96.7 | 90 | 86.7 |
| 37 | La | 100.0 | 95 | 95.4 |

[1]Reaction temperature 340° C.
[2]Reaction temperature 385° C.

EXAMPLE 38

High air ratios with different potassium catalyst.

A catalyst of 80% $W_{0.5}K_{0.5}Ni_{2.5}Co_{4.5}Fe_3BiMo_{12}O_x$ and 20% $SiO_2$ was prepared as described in Example 9 except that five times the potassium was added. Using the mixture of butene-2 above in a ratio of air-to-butene-2 of 31, an apparent contact time of one second and a temperature of 385° C. this catalyst was tested for the production of butadiene. The conversion of the butene-2 was 96.4%, the selectivity was 91% and the single pass yield was 88.1%.

EXAMPLE 39

Oxydehydrogenation of isoamylene.

With the catalyst of Example 13, in a reactor having a reaction zone of 5 cc. a mixture of equal volumes of 2-methylbutene-1 and 2-methylbutene-2 was oxydehydrogenated to give isoprene. At 400° C. and an apparent contact time of two seconds, the conversion of the isoamylene was 85.9%, the selectivity to isoprene was 82% and the single pass yield to isoprene was 70.2%.

EXAMPLE 40

Preparation of isoprene with Cr catalyst.

In the same manner shown by Example 39, the catalyst of Example 1 was used to prepare isoprene. The conversion was 86.2%, the selectivity was 70%, and the single pass yield was 60.5%.

COMPARATIVE EXAMPLES A & B AND EXAMPLES 41–74

Comparison of catalyst containing promoters of invention with base catalyst.

A 5 cc. fixed-bed reactor was constructed of an 8 mm. inside diameter stainless steel tube. Catalysts prepared as described below were charged to the reactor and mg heated to 420° C. under a flow of air. At the reaction temperature for Comparative Example B and Examples 41–74, a reactant composition of propylene/ammonia/oxygen/nitrogen/steam of 1.8/2.2/3.6/2.4/6 was fed over the catalyst at a contact time of three seconds. The WWH (defined as the weight of olefin fed per weight of catalyst per hour) for the reaction was 0.10.

For Comparative Example A, a reactant feed of propylene/ammonia/oxygen/nitrogen/steam in the ratio of 1/1.1/2.1/7.9/4 was used at a temperature of 420° C. A contact time of 6 seconds was used. The WWH was 0.03. This example is included to show a base catalyst operating under normal operating conditions at a low WWH.

The catalysts were prepared as follows:

COMPARATIVE EXAMPLES A AND B

80% $K_{0.1}Ni_{2.5}Co_{4.5}Fe_3BiP_{0.5}Mo_{12}O_x$ + 20% $SiO_2$

A solution of 127.1 g. ammonium heptamolybdate $(NH_4)_6Mo_7O_{24}.4H_2O$ and water was prepared. To this solution was added 6.9 g. of a 42.5% solution of $H_3PO_4$ and 102.7 g. of Nalco 40% silica sol to form a slurry. Separately, an aqueous solution containing 72.7 g., ferric nitrate, $Fe(NO_3)_3.9H_2O$; 29.1 g. bismuth nitrate, $Bi(NO_3)_3.5H_2O$; 78.6 g. cobalt nitrate $Co(NO_3)_2.6H_2O$; 43.6 g. nickel nitrate $Ni(NO_3)_2.6H_2O$; and 6.1 g. of a 10% potassium nitrate solution was prepared. The solution of metal nitrates was slowly added to the slurry. The resulting slurry was evaporated to dryness, and the solid obtained was heated treated at 290° C. for three hours, at 425° C. for three hours and at 550° C. for 16 hours.

EXAMPLE 41

80% $Ge_{0.6}K_{0.1}Ni_{2.5}Co_{4.5}Fe_3BiP_{0.5}Mo_{12}O_x$ + 20% $SiO_2$ 63.56 Grams of ammonium heptamolybdate was dissolved in 60 cc. of warm water. This solution was added to 53.25 g. of Nalco 40% silica sol. The mixture was heated at low heat with constant stirring for about five minutes. To the slurry formed, 3.46 g. of $H_3PO_4$ as a 42.5% solution was added, and the mixture was heated for two minutes.

Separately, 36.36 g. of ferric nitrate was mixed with 10 cc. of water and melted on a hot plate with constant stirring. Squentially 14.55 g. bismuth nitrate, 39.29 g. cobalt nitrate, 21.80 g. of nickel nitrate were added, always waiting until the previous metal nitrate had melted. 3.03 Grams of $KNO_3$ added as a 10% solution was combined, and 1.88 g. of $GeO_2$ was added and melted.

The solution containing metal nitrates was added slowly to the slurry and heating was increased until the mixture started to thicken. The mixture was dried in an oven at 120° C. with occasional stirring. The dried catalyst was calcined at 550° C. for 16 hours.

EXAMPLES 42-66

The other catalysts of the examples were made in an identical manner to the catalysts of Example 41. Germanium, tin, chromium and titanium were added to the catalysts as the oxides. Copper and silver were added to the catalysts as the nitrates. Ruthenium and beryllium were added to the catalysts as the chlorides. Tungsten was incorporated into the catalyst as ammonium tungstate added along with the ammonium heptamolybdate. Although different anions were used, the particular anion of the catalytic component is not deemed to be critical.

In those catalysts not containing phosphorus, the promoter elements of the invention were added to the catalyst through the molybdenum-containing slurry.

EXAMPLE 67

80% $Ga_{1.0}K_{0.1}Ni_{2.5}Co_{4.5}Fe_3BiP_{0.5}Mo_{14}O_x$ + 20% $SiO_2$

In the same manner as described in the examples above, catalyst was prepared using a first slurry containing 24.7 g. ammonium heptamolybdate, 19.4 g. Nalco 40% silica and 1.15 g. of a 42.5% solution of $H_3PO_4$. The second slurry contained 12.1 g. ferric nitrate, 4.8 g. bismuth nitrate, 13.1 g. cobalt nitrate, 7.3 g. nickel nitrate, 1.0 g. of a 10% solution of potassium nitrate and 2.5 g. of gallium nitrate, $Ga(NO_3)_3.3H_2O$. The slurries were combined, evaporated and heat treated as shown above.

EXAMPLE 68

80% $In_{1.0}K_{0.1}Ni_{2.5}Co_{4.5}Fe_3BiP_{0.5}Mo_{13.5}O_x$ + 20% $SiO_2$

A first slurry containing 71.6 g. ammonium heptamolybdate, 58.0 g. of Nalco 40% silica sol and 3.4 g. of a 42.5% solution of phosphoric acid was prepared. A second slurry containing 36.4 g. of ferric nitrate, 14.6 g. bismuth nitrate, 39.3 g cobalt nitrate, 21.8 g. nickel nitrate, 3.0 g. of a 10% solution of potassium nitrate and 4.5 g. of indium chloride was prepared. The slurries were combined, and the solid catalyst was heat treated as described above.

EXAMPLE 69

80% $B_{2.4}W_{0.6}K_{0.1}Ni_{2.5}Co_{4.5}Fe_3BiP_{0.5}Mo_{10.8}O_x$ + 20% $SiO_2$

A slurry of 57.2 g. ammonium heptamolybdate, 4.8 g. ammonium heptatungslate, $(NH_4)_6W_7O_{24}.6H_2O$, 4.5 g. boric acid 3.5 g. of a 42.5% solution of phosphoric acid and 52.3 g. of Nalco 40% silica sol was prepared. To this slurry was added a solution of 36.4 g. ferric nitrate, 14.6 g. bismuth nitrate, 39.3 cobalt nitrate, 21.8 g. nickel nitrate and 3.0 g. of a 10% solution of potassium nitrate. The resulting slurry was evaporated and the solid was heat treated as described above.

The results of the experiments in the ammoxidation of propylene to produce acrylonitrile are shown in Table IV. The parentheses used in Table IV have no significance other than to emphasize the differences in the catalysts.

Table V

Preparation of Acrylonitrile
Comparison of Catalysts of Invention
with Base Catalyst

| Example | Active Ingredients of Catalyst | Single Pass Yield, % |
|---|---|---|
| Comp. A | $(K_{0.1}Ni_{2.5}Co_{4.5}Fe_3BiP_{0.5}Mo_{12}O_x)$ | 80.1* |
| Comp. B | $(K_{0.1}Ni_{2.5}Co_{4.5}Fe_3BiP_{0.5}Mo_{12}O_x)$ | 73.1 |
| 41 | $Ge_{0.6}(K_{0.1}Ni_{2.5}Co_{4.5}Fe_3BiP_{0.5}Mo_{12}O_x)$ | 80.7 |
| 42 | $Ge_{1.0}(K_{0.1}Ni_{2.5}Co_{4.5}Fe_3BiP_{0.5}Mo_{12}O_x)$ | 76.4 |
| 43 | $Sn_{0.5}(K_{0.1}Ni_{2.5}Co_{4.5}Fe_3BiP_{0.5}Mo_{12}O_x)$ | 75.7 |
| 44 | $Sn_{1.0}(K_{0.1}Ni_{2.5}Co_{4.5}Fe_3BiP_{0.5}Mo_{12}O_x)$ | 75.0 |
| 45 | $Cu_{0.1}(K_{0.1}Ni_{2.5}Co_{4.5}Fe_3BiP_{0.5}Mo_{12}O_x)$ | 77.9 |
| 46 | $Ag_{0.1}(K_{0.1}Ni_{2.5}Co_{4.5}Fe_3BiP_{0.5}Mo_{12}O_x)$ | 74.2 |

Table V-continued
Preparation of Acrylonitrile
Comparison of Catalysts of Invention with Base Catalyst

| Example | Active Ingredients of Catalyst | Single Pass Yield, % |
|---|---|---|
| 47 | $Cr_{0.5}(K_{0.1}Ni_{2.5}Co_{4.5}Fe_3BiP_{0.5}Mo_{12}O_x)$ | 78.3 |
| 48 | $Ru_{0.1}(K_{0.1}Ni_{2.5}Co_{4.5}Fe_3BiP_{0.5}Mo_{12}O_x)$ | 76.4 |
| 49 | $Ti_{0.5}(K_{0.1}Ni_{2.5}Co_{4.5}Fe_3BiP_{0.5}Mo_{12}O_x)$ | 74.3 |
| 50 | $Cu_{0.1}Ge_{0.6}(K_{0.1}Ni_{2.5}Co_{4.5}Fe_3BiP_{0.5}Mo_{12}O_x)$ | 76.2 |
| 51 | $Ag_{0.1}Ge_{0.6}(K_{0.1}Ni_{2.5}Co_{4.5}Fe_3BiP_{0.5}Mo_{12}O_x)$ | 75.4 |
| 52 | $Ru_{0.1}Ge_{0.6}(K_{0.1}Ni_{2.5}Co_{4.5}Fe_3BiP_{0.5}Mo_{12}O_x)$ | 79.3 |
| 53 | $Cu_{0.1}B_{1.0}(K_{0.1}Ni_{2.5}Co_{4.5}Fe_3BiP_{0.5}Mo_{12}O_x)$ | 76.7 |
| 54 | $Ag_{0.1}B_{1.0}(K_{0.1}Ni_{2.5}Co_{4.5}Fe_3BiP_{0.5}Mo_{12}O_x)$ | 75.8 |
| 55 | $Ru_{0.1}B_{1.0}(K_{0.1}Ni_{2.5}Co_{4.5}Fe_3BiP_{0.5}Mo_{12}O_x)$ | 76.5 |
| 56 | $Cr_{0.6}W_{0.6}(K_{0.1}Ni_{2.5}Co_{4.5}Fe_3BiP_{0.5}Mo_{10.8}O_x)$ | 73.7 |
| 57 | $Ge_{1.0}(K_{0.1}Ni_{2.5}Co_{4.5}Fe_2BiP_{0.5}Mo_{12}O_x)$ | 79.1 |
| 58 | $Cr_{0.5}Ge_{1.0}(K_{0.1}Ni_{2.5}Co_{4.5}Fe_2BiP_{0.5}Mo_{12}O_x)$ | 79.2 |
| 59 | $Sn_{1.0}(K_{0.1}Ni_{2.5}Co_{4.5}Fe_2BiP_{0.5}Mo_{12}O_x)$ | 76.6 |
| 60 | $W_{0.5}Ge_{1.0}(K_{0.1}Ni_{2.5}Co_{4.5}Fe_2BiMo_{12}O_x)$ | 78.4 |
| 61 | $Cr_{0.5}(K_{0.1}Ni_{2.5}Co_{4.5}Fe_3BiMo_{12}O_x)$ | 79.5 |
| 62 | $W_{0.5}(K_{0.1}Ni_{2.5}Co_{4.5}Fe_3BiMo_{12}O_x)$ | 81.6 |
| 63 | $Ti_{0.5}(K_{0.1}Ni_{2.5}Co_{4.5}Fe_3BiMo_{12}O_x)$ | 78.6 |
| 64 | $Cu_{0.1}B_{0.5}(K_{0.1}Ni_{2.5}Co_{4.5}Fe_3BiMo_{12}O_x)$ | 80.2 |
| 65 | $Sn_{0.5}(K_{0.1}Ni_{2.5}Co_{4.5}Fe_2BiMo_{12}O_x)$ | 80.6 |
| 66 | $Ge_{0.5}(K_{0.1}Ni_{2.5}Co_{4.5}Fe_3BiMo_{12}O_x)$ | 79.1 |
| 67 | $Ga_{1.0}K_{0.1}Ni_{2.5}Co_{4.5}Fe_3BiP_{0.5}Mo_{14}O_x$ | 76.1 |
| 68 | $In_{1.0}K_{0.1}Ni_{2.5}Co_{4.5}Fe_3BiP_{0.5}Mo_{13.5}O_x$ | 76.1 |
| 69 | $B_{2.4}W_{0.6}K_{0.1}Ni_{2.5}Co_{4.5}Fe_3BiP_{0.5}Mo_{10.8}O_x$ | 75.7 |

*WWH is 0.03

Thus, it is seen from the examples above that high per pass conversions at high WWH values are obtained using the catalysts of the invention.

Examples 70–76

Ammoxidation of Propylene
Various catalysts of the invention were prepared as follows:

EXAMPLE 70

80% $Mn_{0.5}K_{0.1}Ni_{2.5}Co_{4.5}Fe_3BiMo_{12}O_x$ and 20% $SiO_2$

The same procedure was used as Comparative Examples A and B, except that 10.74 g. of a 50 wt. % solution of $Mn(NO_3)_2$ was used instead of the phosphorus.

EXAMPLE 71

80% $Th_{0.5}K_{0.1}Ni_{2.5}Co_{4.5}Fe_3BiMo_{12}O_x$ and 20% $SiO_2$

The same procedure was used as above except that 16.56 g. of $Th(NO_3)_4 \cdot 4H_2O$ was used instead of the phosphorus.

EXAMPLE 72

80% $Zr_{0.5}K_{0.1}Ni_{2.5}Co_{4.5}Fe_3BiMo_{12}O_x$ and 20% $SiO_2$

The same procedure was used except that 9.68 g. of $ZrOCl_2 \cdot 8H_2O$ was used instead of the phosphorus.

EXAMPLE 73

80% $Y_{0.5}K_{0.1}Ni_{2.5}Co_{4.5}Fe_3BiMo_{12}O_x$ and 20% $SiO_2$

The same procedure was used except that 10.96 g. of $Y(NO_3)_3 \cdot 5H_2O$ was used instead of the phosphorus.

The catalysts were ground and screened to give 20 to 35 mesh fraction that was charged to a 5 cc. reaction zone of a tubular reactor constructed of stainless steel. The ammoxidation was carried out using a feed of propylene/ammonia/oxygen/nitrogen/steam of 1.8/2.2/3.6/2.4/6. The temperature of the bath surrounding the reactor was maintained at 420° C., and the apparent contact time was three seconds.

The results of these experiments are given in Table V.

TABLE VI
Ammoxidation of Propylene Using $A_{0.5}K_{0.1}Ni_{2.5}Co_{4.5}Fe_3BiMo_{12}O_x$

| | | Results, % | | |
|---|---|---|---|---|
| Example | Catalyst, A= | Conversion | Selectivity | Single Pass Yield |
| 70 | Mn | 99.6 | 82 | 81.8 |
| 71 | Th | 94.2 | 83 | 78.2 |
| 72 | Zr | 98.8 | 77 | 76.3 |
| 73 | Y | 99.6 | 74 | 73.9 |

EXAMPLES 74–77

Ammoxidation of isobutylene.

In the same manner described above, various catalysts were prepared and tested in the ammoxidation of isobutylene to methacrylonitrile. The reactions were run at 400° C. using a feed of isobutylene/ammonia/air/steam of 1/1.5/11/4. The apparent contact time was three seconds. All catalysts contained 20% $SiO_2$. The results are given in Table VI based on methacrylonitrile.

Table VII
Ammoxidation of Isobutylene to Methacrylonitrile with $A_qNi_{2.5}Co_{4.5}Fe_3BiMo_{12}O_x$

| | | Results, % | | |
|---|---|---|---|---|
| Example | Catalyst A = | Conversion | Selectivity | Single Pass Yield |
| 74 | $Mn_{0.5}Cs_{0.1}$ | 99.8 | 75 | 74.9 |
| 75 | $Cr_{0.5}Cs_{0.1}$ | 100.0 | 79 | 79.0 |
| 76 | $Ge_{0.5}Cs_{0.1}$* | 97.0 | 77 | 74.7 |
| 77 | $W_{0.5}Cs_{0.1}$** | 96.0 | 74 | 71.4 |

*additional heat treatment of catalyst at 650° C. for two hours.
**same as * plus run at 410° C.

EXAMPLE 78

Ammoxidation of propylene.
A catalyst of $CrW_{0.5}K_{0.1}Ni_{2.5}Co_{4.5}Fe_2BiMo_{12}O_x$ was prepared and heat treated at 550° C. for 18 hours and at 600° C. for two hours. The ammoxidation of propylene was conducted in a 5 cc. reactor at a temperature of 440° C., and a contact time of three seconds and a WWH of 0.10 using a feed of propylene/ammonia/oxygen/nitrogen/steam of 1.8/2.2/3.6/2.4/6. The conversion of the propylene was 96.8%, the selectivity to acrylonitrile was 86% and the single pass yield of acrylonitrile was 83.2%.

EXAMPLE 79

Ammoxidation of propylene.

In the same manner as described in Example 78, a catalyst of 80% $MnCr_{0.5}K_{0.1}Ni_{2.5}Co_{4.5}Fe_2BiMo_{12}O_x$ and 20% $SiO_2$ was prepared and heat treated at 550° C. for 16 hours and at 600° C. for two hours. When the catalyst was used in the preparation of acrylonitrile, the conversion of the propylene was 99.0%, the selectivity to acrylonitrile was 85.6% and the single pass yield was 84.7%.

EXAMPLE 80

Ammoxidation of propylene.

In the same manner as described in Example 78 a catalyst of 80% $GeW_{0.5}K_{0.1}Ni_{2.5}Co_{4.5}Fe_2BiMo_{12}O_x$ and 20% $SiO_2$ was prepared and heat treated at 550° C. for 16 hours. The conversion of the propylene was 97.8%, the selectivity was 85.1% and the single pass yield was 83.1%.

EXAMPLE 81

Ammoxidation of propylene.

In the same manner as described for Example 79, a catalyst of 80% $PrW_{0.5}K_{0.3}Ni_{2.5}Co_{4.5}Fe_2BiMo_{12}O_x$ and 20% $SiO_2$ was prepared and used in the ammoxidation of propylene. The propylene was 99.2% converted, the single pass yield was 82.7% and the selectivity was 83%.

EXAMPLE 82

Ammoxidation of propylene.

In the same manner as shown in Example 80, a catalyst of 80% $MnSb_{0.5}K_{0.1}Ni_{2.5}Co_{4.5}Fe_2BiMo_{12}O_x$ and 20% $SiO_2$ was prepared and tested except that the reaction temperature was 420° C. The conversion of the propylene was 100%, and the single pass yield and selectivity were 80.4%.

EXAMPLES 83-90

Fluid-bed ammoxidation.

In a 1½″ internal diameter fluid-bed reactor with sieve trays, the ammoxidation of propylene using various catalysts of the invention containing 20% silica was conducted. The catalysts were heat treated at 550° C. for 16 hours and then an additional heat treatment for two hours at the temperature shown in Table VII was given. The reactor was charged with 395 cc. of catalyst. The feed of propylene/ammonia/air was 1/1.2/10.5, the WWH was 0.12, the pressure was 12 p.s.i.g. and the contact time was 5.5 seconds. The catalysts employed and the results are shown in Table VII.

Table VIII

Ammoxidation of Propylene in Fluid-Bed Reactor Using Catalyst of $A_aK_{0.1}Ni_{2.5}Co_{4.5}Fe_2BiMo_{12}O_x$

| Example | Catalyst, $A_a=$ | Heat Treat., °C. | Reaction Temp., °C. | Conversion | Selectivity | Single Pass Yield |
|---|---|---|---|---|---|---|
| 83 | $W_{0.5}Fe$ | 625 | 420 | 96.3 | 79 | 76.1 |
| 84 | $W_{0.5}Fe$ | ″ | 435 | 99.7 | 78 | 77.8 |
| 85 | $Cr_{0.5}Fe$ | ″ | ″ | 97.7 | 79 | 77.2 |
| 86 | $Cr_{0.5}Fe$ | ″ | 445 | 98.7 | 79 | 78.0 |
| 87 | $MnCr_{0.5}$ | 600 | 435 | 95.9 | 83 | 79.6 |
| 88 | $MnCr_{0.5}$ | ″ | 445 | 97.7 | 83 | 81.1 |
| 89 | $CrW_{0.5}$ | ″ | 435 | 96.2 | 84 | 80.5 |
| 90 | $CrW_{0.5}$ | ″ | 445 | 97.9 | 83 | 81.3 |

EXAMPLES 91-101

Oxidation of isobutylene at atmospheric pressure.

Various catalysts of the invention were prepared by the procedures described above.

In a fixed-bed reactor, constructed of a 0.8 cm. inside diameter stainless steel tube, was placed 5 cc. of each of the catalysts prepared above. These catalysts were tested at a reaction temperature of 371° C. using a feed of isobutylene/air/steam of 1/10/4 and an apparent contact time of four seconds. The results of these experiments are given in Table VIII.

Table IX

Oxidation of Isobutylene to Methacrolein and Methacrylic Acid at Atmospheric Pressure Using a Catalyst of $A_aNi_{2.5}Co_{4.5}Fe_3BiMo_{12}O_x$

| | | Results, % | | | | |
|---|---|---|---|---|---|---|
| | | Single Pass Yield | | | | |
| Example | Catalyst | MA | MAA | Total | Conv. | Select. |
| 91 | $Pr_{0.5}K_{0.1}$ | 61.6 | 2.2 | 63.8 | 91.3 | 69.9 |
| 92 | $Mn_{0.5}K_{0.1}$ | 68.5 | 2.9 | 71.4 | 100.0 | 71.4 |
| 93 | $Ge_{0.5}K_{0.1}$ | 67.0 | 4.5 | 71.5 | 100.0 | 71.5 |
| 94 | $Nb_{0.5}K_{0.1}$ | 52.2 | 2.5 | 54.7 | 82.9 | 66.1 |
| 95 | $Th_{0.5}K_{0.1}$ | 74.3 | 2.6 | 76.9 | 100.0 | 76.9 |
| 96 | $Sb_{0.5}K_{0.1}Cu_{0.1}$ | 66.1 | 1.4 | 67.5 | 100.0 | 67.5 |
| 97 | $Cr_{0.5}Cs_{0.5}$ | 58.9 | 2.9 | 61.8 | 81.7 | 75.6 |
| 98 | $Mn_{0.5}Cs_{0.5}K_{0.5}$ | 68.3 | 3.4 | 71.7 | 100.0 | 71.7 |
| 99 | $Ge_{0.5}Cs_{0.5}K_{0.5}$ | 77.1 | 1.0 | 78.1 | 94.3 | 82.9 |
| 100 | $Nb_{0.5}Cs_{0.5}K_{0.5}$ | 75.3 | 1.2 | 76.5 | 94.7 | 80.8 |
| 101 | $Sb_{0.5}Cs_{0.5}S_{0.25}$ | 74.1 | 1.0 | 75.1 | 91.4 | 82.1 |

MA = Methacrolein
MAA = Methacrylic acid
*12 p.s.i.g.

EXAMPLES 102-106

Oxidation of isobutylene at superatmospheric pressure.

In the same manner as described above in Examples 91-101, various catalysts prepared above were used in reactions at superatmospheric pressure. The pressure, unless otherwise noted, was 12 p.s.i.g. The temperature of the reaction and the results are shown in Table X. The feed was of the same composition as described above and the apparent contact time was 3.5-4 seconds and the WWH was 0.098-0.159.

Table X

Oxidation of Isobutylene to Methacrolein and Methacrylic Acid at Superatmospheric Pressure in the Presence of a Catalyst of $A_aNi_{2.5}Co_{4.5}Fe_3BiMo_{12}O_x$

| Example | Catalyst, $A_a$ = | Temp., °C. | Yield Per Pass MA | MAA | Total | Conversion | Selectivity |
|---|---|---|---|---|---|---|---|
| 102 | $Ge_{0.5}Cs_{0.5}$ | 371 | 68.4 | 5.6 | 74.0 | 96.5 | 76.7 |
| 103 | $Mn_{0.5}Cs_{0.1}$ | 343 | 64.5 | 4.8 | 69.3 | 99.6 | 69.5 |
| 104 | $Th_{0.5}Cs_{0.5}$ | 343 | 61.5 | 3.5 | 65.0 | 89.0 | 73.0 |
| 105 | $Ce_{0.5}Cs_{0.2}$ | 363 | 70.3 | 6.4 | 76.7 | 98.9 | 77.6 |
| 106* | $Sb_{0.5}Cs_{0.5}S_{0.25}$ | 371 | 77.2 | 1.6 | 78.8 | 92.8 | 85.0 |

9.7 p.s.i.g.

EXAMPLE 107

Ammoxidation of propylene.

In the same manner as shown in Example 41 a catalyst of $Ta_{0.5}K_{0.1}Ni_{2.5}Co_{4.5}Fe_3BiMo_{12}O_x$ was prepared and tested in the ammoxidation of propylene. The single pass yield was 78.8%, the selectivity was 81% and the conversion of the propylene was 97.4%.

We claim:

1. Catalysts of the formula:

$$X_aA_bD_cE_dFe_fBi_gMo_{12}O_x$$

wherein X is Y, Zr, S, Th or mixture thereof;
A is an alkali metal, thallium or mixture thereof;
D is nickel, cobalt, calcium, strontium, cadmium, or mixture thereof;
E is phosphorus, arsenic, boron, antimony or mixture thereof; and wherein
a is greater than 0 and less than 5;
b and d are 0–4;
c is 0.1 to 20;
f and g are 0.1–10; and
x is the number of oxygens required to satisfy the valence requirements of the other elements present, said catalyst being free of chromium.

2. The catalyst of claim 1 wherein X is yttrium.
3. The catalyst of claim 1 wherein X is zirconium.
4. The catalyst of claim 1 wherein X is sulfur.
5. The catalyst of claim 1 wherein X is thorium.
6. The catalyst of claim 1 wherein X is yttrium, zirconium or sulfur.
7. The catalyst of claim 1 wherein said catalyst contains thorium and cesium.
8. Catalysts of the formula $$Ge_aA_bD_cE_dFe_fBi_gMo_{12}O_x$$

A is an alkali metal or mixture thereof;
D is nickel, cobalt, calcium, strontium, cadmium or mixture thereof;
E is phosphorus, arsenic, boron, or mixture thereof; and wherein
a is greater than 0 and less than 5;
b is greater than 0 but less than 4.
c is 0.1–20;
d is 0–4;
f and g are 0.1–10; and
x is the number of oxygens required to satisfy the valence requirements of the other elements present, said catalysts being free of antimony and chromium.

9. Catalysts of the formula:

$$X_aA_bD_cE_dFe_fBi_gMo_{12}O_x$$

wherein
X is Y, Zr, S, Th, or mixture thereof;
A is an alkali metal, thallium or mixture thereof;
D is nickel, cobalt, magnesium, calcium, strontium, zinc, cadmium or mixture thereof;
E is phosphorus, arsenic, boron, tungsten, antimony or mixture thereof; and wherein
a is greater than 0 and less than 5;
b and d are 0–4;
c is 0.1–20;
f and g are 0.1–10; and
x is the number of oxygens required to satisfy the valence requirements of the other elements present, said catalyst being free of antimony and chromium.

10. The catalyst of claim 9 wherein X is yttrium, zirconium or sulfur.

11. Catalyst of the formula:

$$Ge_aA_bD_cE_dFe_fBi_gMo_{12}O_x$$

A is an alkali metal or mixture thereof;
D is nickel, cobalt, magnesium, calcium, strontium, zinc, cadmium or mixture thereof;
E is phosphorus, arsenic, boron, tungsten, antimony or mixture thereof; and wherein
a is greater than 0 and less than 5;
b is greater than 0 but less than 4;
c is 0.1–20;
d is 0–4;
f and g are 0.1–10; and
x is the number of oxygens required to satisfy the valence requirements of the other elements present, said catalyst being free of antimony and chromium.

12. The catalyst of claim 11 wherein said catalyst contains germanium and cesium.

13. The catalyst of claim 12 wherein said catalyst further contains potassium.

14. Catalysts of the formula:

$$y_aA_bD_cE_dFe_fBi_gMo_{12}O_x$$

wherein X is Y, Zr, Ag, S, Ce, Th, Pr, Ru, Ga, La or mixtures thereof
D is nickel, cobalt, magnesium, calcium, strontium, zinc, cadmium or mixture thereof;
E is phosphorus, arsenic, boron, tungsten, antimony or mixture thereof with the proviso that when X is Ce, Pr or La, D is Mg, Ca, Si, Zn, Cd or mixtures thereof and the further proviso that when X is Ag, Ru or Ga, D is Sr; and wherein
a is greater than 0 and less than 5;
b is greater than 0 but less than 4;
c is 0.1–20;
d is 0–4;
f and g are 0.1–10; and
x is the number of oxygens required to satisfy the valence requirements of the other elements present.

15. The catalyst of claim 14 wherein X is yttrium, zirconium, silver, sulfur, cerium, praseodynium, ruthenium, gallium,,lanthanum or mixtures thereof.

16. Catalysts of the formula:

$$In_aA_bSr_cE_dFe_fBi_gMo_{12}O_x$$

wherein
A is an alkali metal or mixture thereof:
E is phosphorus, arsenic, boron, tungsten, antimony or mixtures thereof and wherein
a is greater than 0 and less than 5;
b is greater than 0 and less than 4;
c is 0.1 to 20;
d is 0–4;
f and g are 0.1–10; and
x is the number of oxygens required to satisfy the valence requirements of the other elements present.

17. Catalyst of the formula $$X_aA_bD_cE_dFe_fBi_gMo_{12}O_x$$

wherein
A is an alkali metal, thallium or mixtures thereof;
D is Ni, Co, Mg, Sr, Ca, Zn, Cd or mixtures thereof;
E is P, As, B, Sb or mixtures thereof;
X is Y, Zr, Ag, S, Ce, Th, Pr, Ru, Ga, Nb, Ge, Cr, Sn, Mn, In, Cu, W, Ta, Te, La or mixtures thereof; and wherein
a is greater than 0 and less than 5;
b and d are 0–4;
c is 0.1 to 20;
f and g are 0.1–10; and
x is the number of oxygens required to satisfy the valence requirements of the other elements present; and wherein E and X are so selected that said catalyst contains a two or more element system selected from the group consisting of Mn+Sb, Mn+Cr, Pr+W or Mn+Ge.

18. The catalyst of claim 17 wherein said catalyst contains Mn+Sb.

19. The catalyst of claim 17 wherein said catalyst contains Mn+Cr.

20. The catalyst of claim 17 wherein said catalyst contains Pr+W.

21. The catalyst of claim 17 wherein said catalyst contains Mn+Ge.

* * * * *